United States Patent [19]

Krasner et al.

[11] Patent Number: 4,676,228

[45] Date of Patent: Jun. 30, 1987

[54] MEDICAL APPARATUS HAVING INFLATABLE CUFFS AND A MIDDLE EXPANDABLE SECTION

[76] Inventors: Jerome L. Krasner, 638 Main St., Ashland, Mass. 01721; John P. DiBenedetto, 58 Winslow Ave., Norwood, Mass. 02062

[21] Appl. No.: 791,219

[22] Filed: Oct. 25, 1985
(Under 37 CFR 1.47)

[51] Int. Cl.$^4$ .............................................. A61B 1/00
[52] U.S. Cl. ......................................... 128/4; 604/101
[58] Field of Search ............... 128/4, 6, 348.1, 325; 604/101

[56] References Cited

U.S. PATENT DOCUMENTS

| | | | |
|---|---|---|---|
| 550,238 | 11/1895 | Allen, Jr. | |
| 2,687,131 | 8/1954 | Raiche | 128/349 |
| 2,767,705 | 10/1956 | Moore | 128/4 |
| 2,854,982 | 10/1958 | Pagano | 128/348 |
| 2,855,934 | 10/1958 | Daughaday, Jr. | 128/349 |
| 2,936,760 | 5/1960 | Gants | 128/349 |
| 3,045,677 | 7/1962 | Wallace | 128/349 |
| 3,050,066 | 8/1962 | Koehn | 128/349 |
| 3,144,868 | 8/1964 | Vascalevich | 128/350 |
| 3,631,848 | 1/1972 | Muller | 128/348 X |
| 3,882,852 | 5/1975 | Sinnreich | 128/4 |
| 3,895,637 | 7/1975 | Choy | 128/348 |
| 4,066,070 | 1/1978 | Utsugi | 128/4 |
| 4,148,307 | 4/1979 | Utsugi | 128/4 |
| 4,176,662 | 12/1979 | Frazer | 128/6 |
| 4,180,076 | 12/1979 | Betancourt | 604/101 |
| 4,198,981 | 4/1980 | Sinnreich | 604/101 X |
| 4,207,872 | 6/1980 | Meiri et al. | 128/4 |
| 4,224,929 | 9/1980 | Furihata | 128/6 X |
| 4,295,464 | 10/1981 | Shirata | 128/328 X |
| 4,404,971 | 9/1983 | Leveen et al. | 128/348.1 |
| 4,448,188 | 5/1984 | Loeb | 128/6 |
| 4,456,011 | 6/1984 | Warnecke | 128/325 |
| 4,577,621 | 3/1986 | Patel | 128/4 |

OTHER PUBLICATIONS

*NASA Technical Briefs*, Winter 1978, "Self-Propelling Self-Locating Colonoscope", pp. 563–564, Frazer, Robert E.

*Colonoscopy, Diagnosis and Treatment of Colonic Diseases* by Hiromi Shinya, Igaku-Shoin, of New York, N.Y. and Tokyo, Japan (1982), pp. 69–76 and 194.

*Primary Examiner*—William H. Grieb
*Attorney, Agent, or Firm*—Schiller, Pandiscio & Kusmer

[57] ABSTRACT

An improved medical device for use with an elongated flexible instrument of the type adapted to at least partially extend into the lumen of a tubular body part and having a front end for leading said instrument through said lumen and a rear end opposite said front end. The device comprises (a) an elongated flexible sheath capable of being coaxially mounted on and axially slidable with respect to said instrument between said front and rear ends of said instrument and (b) an integrally-formed cuff assembly including a front inflatable cuff section adapted to be secured to the front end of said instrument, a rear inflatable cuff section adapted to be secured to the front end of said sheath and a middle expandable section integrally formed with said front and rear cuff sections for protecting that portion of said instrument between the position of said front and rear cuffs.

13 Claims, 4 Drawing Figures

MEDICAL APPARATUS HAVING INFLATABLE CUFFS AND A MIDDLE EXPANDABLE SECTION

The present invention relates generally to medical apparatus, and more particularly, to an improved apparatus for more easily and safely navigating a medical instrument, such as an endoscope, through the lumen of a tubular body part, such as the large intestines.

Generally, it is well-known to make instruments, designed to be inserted into a living tubular body part, such as the urethra, esophagus, stomach, small intestines, and large intestines, as an elongated flexible device so that the instrument can navigate through the lumen of the portion of the particular body part without perforating the walls of the particular body part. These flexible instruments have been known to include selectively inflatable elastic cuffs or balloons to position and/or navigate the instruments through a particular body part. For examples of such instruments see U.S. Pat. Nos. 550238; 2687131; 2854982; 2855934; 2936760; 3045677; 3050066; 3144868; 3631848; 3882852; 3895637; 4066070; 4148307; 4176662; 4180076; 4198981; 4224929; 4295464; 4404971; 4448188 and 4456011. Also see Frazer, Robert E.; "Self-Propelling, Self-Locating Colonoscope"; NASA Tech Briefs, Winter 1978, pages 563 and 564. One such instrument is the flexible elongated endoscope, typically including fiber optics suitably encased in a cladding material, so as to form a fiber optic bundle. An objective lens is usually placed in front of the bundle. The fiber optic bundle and lens are fixedly secured within an elongated flexible sheath. See, for example, U.S. Pat. Nos. 4066070; 4148307; 4176662; 4224929 and the Frazer article. The flexible elongated endoscope is often used as an instrument for viewing, as well as conveying light and selected radiation (from a laser, for example) to the interior of the body part. The flexible fiber optic bundle and sheath are sufficiently flexible to allow navigation of the instrument through the lumen of the particular tubular body part.

Endoscopic instruments employing inflatable elastic cuffs are particularly useful in examining the large intestines since these instruments can be inserted through the anus and navigated through the intestines, against peristaltic action. The colonic endoscope must be carefully navigated through the large intestines in order to avoid perforating the colonic walls. This is usually accomplished by pushing the instrument up through the organ and twisting the instrument in order to turn the instrument around sharp turns, such as the hepatic flexure, where the ascending colon bends into the transverse colon, splenic flexure, where the transverse colon bends into the descending colon, and the sigmoid flexure, where the descending colon is convoluted before forming the rectum. In this way, the instrument can be used to examine the lumen of any part of the large intestines from the cecum to the rectum. The endoscopic instruments employing elastic inflatable cuffs are, therefore, made so that the sheathed instrument and the cuffs in their deflated state should be of a small diameter compared to that of the lumen of the large intestines to make the pushing and twisting of the instrument as easy as possible. Although the instruments are relatively flexible so that they can be twisted and turned around these portions of the large intestines, they, nevertheless, must be sufficiently stiff to be pushed forward. When the endoscopist wishes to observe and/or treat a particular location of the colon, the endoscopist inflates the cuff so that the cuff radially expands in all directions and grips the interior surfaces of the colon so as to hold the instrument in place. Air can then be pumped into the area of and expand the colon in order to improve the visibility of and accessibility to, the colonic walls.

Examples of such systems are shown, for example, in U.S. Pat. No. 4224929, wherein two axially spaced inflatable cuffs are used to create a space so that forceps can be used to excise material from the colonic wall therebetween. U.S. Pat. Nos. 4066070; 4148307; 4176662 and the Frazer article suggest that the inflatable cuffs can also be used to help push the instrument through the lumen of the large intestine. Specifically, U.S. Pat. Nos. 4066070 and 4148307 each suggest an assembly of cuffs (two and three cuffs, respectively) for each such use. In U.S. Pat. No. 4176662 and the Frazer article, a first inflatable annular cuff is fixedly secured to the sheath of the instrument. A second inflatable annular cuff, similar to the first cuff, is mounted on the sheath of the instrument behind the first cuff and axially slidable on the sheath toward and away from the front cuff. An expandable bellows is secured between and to both cuffs so that by selectively inflating the cuffs and bellows the instrument is pushed through the lumen of the large intestines. Specifically, with the front cuff deflated, the rear cuff is inflated so that it contracts and is securely held by the interior surfaces of the lumen. Air is transmitted into the bellows, causing the latter to expand so as to push the front cuff and thus the instrument forward. The front cuff can then be inflated and the rear cuff deflated. By withdrawing air from the bellows, the rear cuff is pulled toward the front cuff since it is free to slide on the external sheath of the instrument.

With all of the foregoing instruments, colonoscopies are still not performed routinely since pushing the instrument through the large intestines requires a great deal of skill so as not to perforate the intestine walls.

An improved instrument is described in co-pending application U.S. Ser. No. 740,171, filed May 31, 1985 in the names of James E. Lyddy, Jr.; William Z. Penland and Dr. Paul H. Sugarbaker, assigned to the United States Government and licensed to the assignee of the present application. The device includes an assembly comprising an elongated flexible sheath adapted to be mounted on and axially slidable on an elongated, flexible endoscopic instrument, a front cuff adapted to be mounted on the front end of the instrument and a rear cuff adapted to be mounted on the sheath so as to be movable with the sheath relative to the front cuff. The front and rear cuffs are selectively inflatable and deflatable so that at least a portion of the body part and the corresponding lumen can be straightened with one or both cuffs when the cuff or cuffs are inflated, and so that the instrument can advance through the corresponding lumen, reducing the risk of perforating the wall of the body part.

While the instrument described in the Lyddy et al. application is believed to be an improvement over the prior art devices since, inter alia, portions of the colon are each straightened before the instrument is pushed through the respective portion, various problems were encountered in the use of the device shown in that application. For one, the materials chosen for the cuffs, as well as the stock from which the sheath was made, were not satisfactory.

More specifically, the cuffs are made of a latex material, which apparently had been made in an inefficient dip process resulting in non-uniform composition. Each of these latex cuffs was incapable of completely conforming to the shape of the sheath or endoscopic sheath when deflated so that a portion of each cuff radially protrudes from the instrument. This makes it more difficult to advance the instrument through the colon. The spacing between the cuffs not only exposed the colonoscope to contaminants but creates a problem with maintaining the efficacy of the airway supply tubes. The sheath apparently is made from a solid tube stock to form a long semi-flexible tube having a rigid section at its front end for supporting the rear cuff. The rigid section allows the rear cuff to be inflated without exerting constricting pressure between the sheath and the endoscope. However, when the rear cuff is deflated and the slide advanced, difficulties are encountered in advancing the slide arrangement since the deflated cuff and the leading edge of the rigid section of the sheath tend to catch on the colonic wall as the instrument is advanced through the colon. Further problems are encountered with the connecting air lines which are used to fill and evacuate the cuffs. These lines tend to become entangled and restrict the movement of the instrument through the colon.

Further, the front portion of the sheath, mounted close to the front of the endoscope, must be sufficiently stiff to permit advancement of the endoscope and sheath, while compliant enough to permit remote flexing of the colonoscope to view the colonic wall and to negotiate curves through the intestines, i.e., the sigmoid, hepatic and splenic flexures. Typically, a colonic endoscope is advanced through the rectum into the sigmoid until it reaches an acute angle at the junction of the sigmoid and the descending colon. Often, despite an open lumen ahead, further insertion does not advance the tip of the endoscope, but rather, merely elongates the sigmoid inverted U loop. Advancement of the endoscope is usually accomplished by rotating the colonoscope approximately 360 degrees counterclockwise thereby forming a shortened alpha loop which causes the tip to slide into the descending colon (known as an alpha maneuver). However, further pushing to advance the colonoscope often results in the reelongation of the sigmoid U loop. To overcome this undesirable condition, it is common practice to insert a rigid slide over the colonic endoscope. The slide is sized to extend from the anus to the descending colon and remains in this position so as to prevent the sigmoid U loop from reforming during the remaining examination.

Another approach for providing selective rigidity for specific portions of the intestines is described in U.S. Pat. No. 4176662. Internal spaces of the sheath of the endoscope shown in this patent are provided with material having a sharp melting point slightly above body temperature so that the portions of the endoscope may be made flexible by applying an electric current to separate heating wires disposed in those sections of the sheath in contact with the material. However, such an arrangement requires modification to the endoscope itself, and would not be available with many commercially available endoscopes. Further, the use of heat sensitive material within the endoscope sheath could pose serious problems for a patient should any material leak into the patients body.

It is an object of the present invention to reduce or overcome the above-noted problems of the prior art.

A more specific object of the present invention is to provide an improved instrument of the type described in the co-pending Lyddy et al. application.

Another specific object of the present invention is to provide an improved instrument of the type described in the co-pending Lyddy et al. application, wherein the cuffs are made of a material more easily conformable to the supporting structure.

And another object of the present invention is to provide an improved instrument of the type described in the co-pending Lyddy et al. application, wherein the forward end of the sheath is shaped to minimize interference when advancing the sheath alone or with the endoscope.

And yet another object of the present invention is to provide an improved instrument of the type described in the co-pending Lyddy et al. application in which the airways used to provide air to and from each of the cuffs are constructed to provide little or no interference with the movement of the instrument through the lumen of the body portion.

And still another object of the present invention is to provide an improved instrument of the type described in the co-pending Lyddy et al. application, wherein the portion of the flexible instrument in the space between the forward and rear cuffs will not become contaminated during use.

And yet another object of the present invention is to provide an improved instrument of the type described in the co-pending Lyddy et al. application having safe and effective means for making the the sheath more rigid so that the instrument can be passed through such portions of the intestines as the sigmoid flexure.

These and other objects are achieved by an improved medical device for use with an elongated flexible instrument of the type adapted to at least partially extend into the lumen of a tubular body part and having a front end for leading said instrument through said lumen and a rear end opposite said front end. The device comprises (a) an elongated flexible sheath capable of being coaxially mounted on and axially slidable with respect to said instrument between said front and rear ends of said instrument and (b) an integrally-formed cuff assembly including a front inflatable cuff section adapted to be secured to the front end of said instrument, a rear inflatable cuff section adapted to be secured to the front end of said sheath and a middle expandable section integrally formed with said front and rear cuff sections for protecting that portion of said instrument between the position of said front and rear cuffs.

Other objects of the invention will in part be obvious and will in part appear hereinafter. The invention, accordingly, comprises the apparatus possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings, wherein.

In the drawings, the same numerals are used to refer to similar or identical parts.

Figure 1:
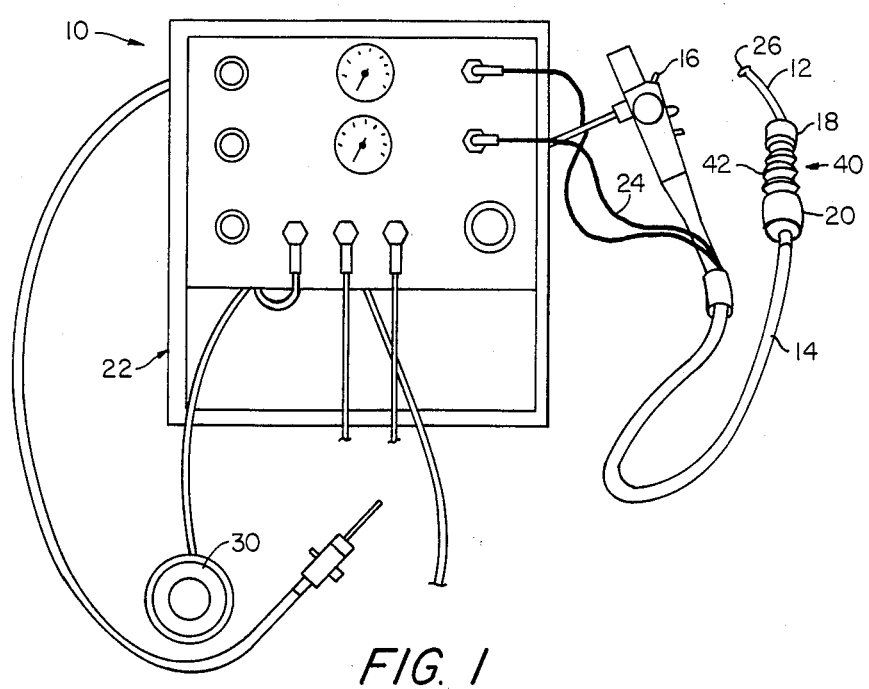
FIG. 1 is a top perspective view of the preferred embodiment of the apparatus of the type shown in the co-pending Lyddy et al. application and modified in accordance with the present invention.
Figure 2:
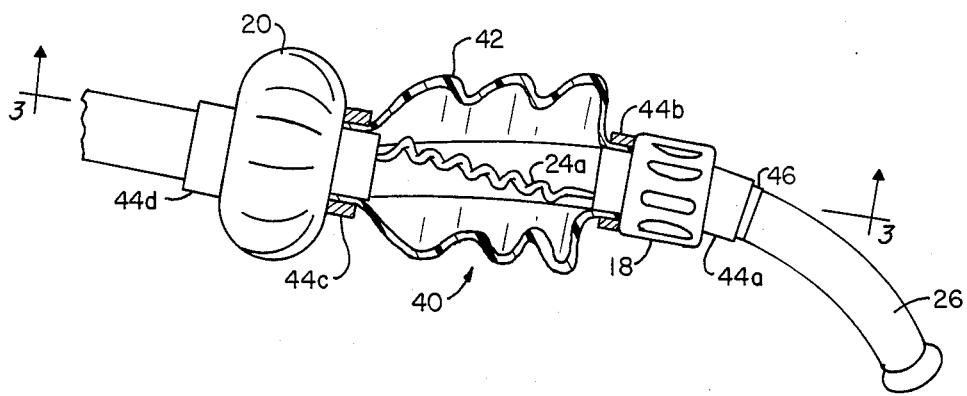
FIG. 2 is a side perspective view, partially cut in section, of the front and forward ends of the sheath and instrument of the apparatus of FIG. 1.
Figure 3:
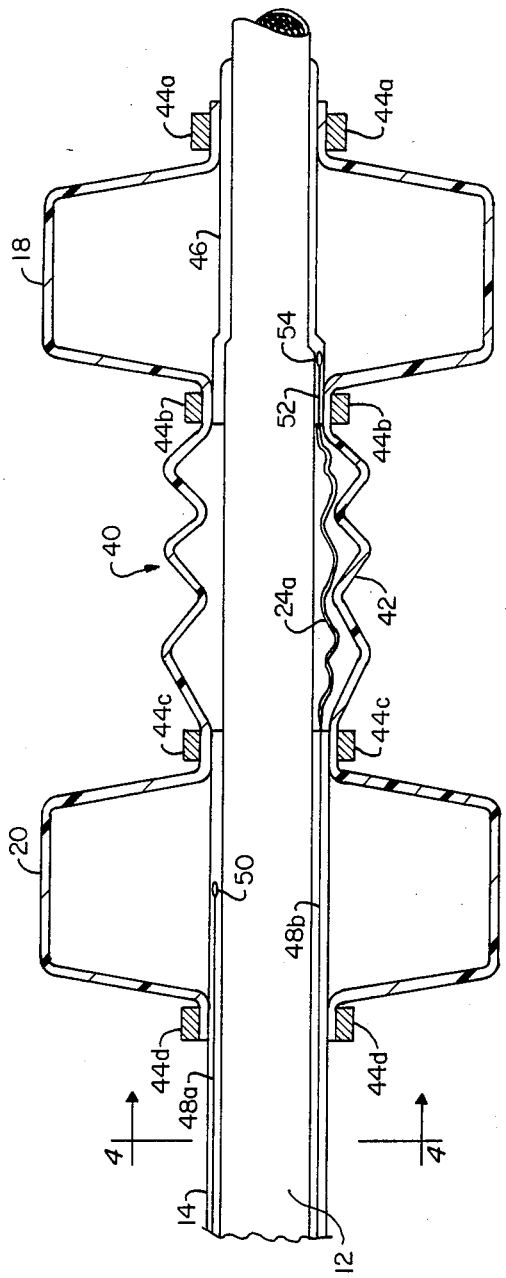
FIG. 3 is a cross-sectional axial view taken along line 3—3 in FIG. 2.

Referring to FIG. 1, the apparatus 10 includes an instrument 12, modified in accordance with the present invention. The instrument 12 is shown in the form of a colonic endoscopic instrument connected to a control section 16. The instrument is disposed within a flexible, axially movable sheath 14, and provided with the front cuff 18; while the sheath 14 is provided with a rear cuff 20. The rear cuff 20 is movable with the sheath with respect to the front cuff 18, and selectively inflated and deflated by the control system 22, in order to straighten the colon so that the instrument can be more easily advanced through the colon, as described in the co-pending Lyddy et al. application.

As described in the co-pending Lyddy et al. application, the cuffs are described as preferably made of latex. Further, the instrument 12 may be any type of elongated flexible instrument, such as a sigmoidoscope or colonoscope. Although not illustrated in detail, such an instrument 12 can include flexible fiber optics suitably encased in a cladding material, so as to form a fiber optic bundle, an objective lens disposed at the forward end of the fiber optic bundle (for defining an image plane and/or an object plane depending on whether the fiber optic bundle is used for transmitting an image from or transmitting radiation to the front of the endoscope) at the front end 26 of the instrument 12. The fiber optic bundle and lens are fixedly secured within an elongated flexible sheath (separate and in addition to the sheath 14), typically made of a relatively soft elastomeric material, such as rubber or neoprene. The instrument 12 can include other devices such as forceps, as shown in U.S. Pat. No. 4224929, and an air conduit for forcing air into the lumen under inspection in order to expand the walls of the colon to provide a better view of the walls.

The control system 22 for selectively inflating and deflating the cuffs 18 and 20 is described in the co-pending Lyddy et al. application. A foot switch 30 is used to sequence the system through the various steps of the operation. Generally, the cuffs are selectively inflated and deflated through a repeatable sequence of the following steps:

Both cuffs are deflated so that the front end of the instrument 12 and sheath 14 can be inserted into the lumen of the tubular body part, as for example, through the anus into the large intestines. Preferably, the instrument 12 and sheath 14 are inserted into the intestines for a certain distance until a certain increased resistance is encountered.

The foot switch 30 is then activated to advance the operation of the system to the next step of the operational sequence. In this step, the front cuff 18 remains deflated and the rear cuff 20 inflates. The rear cuff expands to grip the interior surface of the intestine wall. A gentle retrograde traction is placed on the sheath 14 by the operator at the back end to pull the sheath axially backwards relative to the instrument 12. Pulling the intestines backward with the sheath 14 and inflated rear cuff 20 tends to have the simultaneous effect of tending to straighten the mucosal folds, as well as the general direction of the large intestines (as, for example, at the various flexures of the colon), at least a few centimeters and advance the front end of the instrument 12 with the deflated front cuff 18 in a forward direction through the colon. The front end 26 of the instrument 12 is then pushed forward further through the straightened colon advancing the instrument 12 with the front cuff 18 until resistance is encountered.

The third operating position is then performed by the activation of the foot switch 30. The front cuff 18 will inflate sufficiently in all radial directions so as to grip the intestine walls so that when the rear cuff is subsequently deflated the apparatus will not slip backwards. The rear cuff will then deflate. With the rear cuff deflated the sheath 14 and cuff 20 can now be manually advanced by axially sliding the sheath 14 in a forward direction on the instrument 12. The sheath 14 is advanced until the sheath cannot be further advanced in a direction indicating the rear cuff 20 is adjacent the front cuff 18.

The next operating position accomplished by the activation of the foot switch 30 results in the, front cuff 18 remaining inflated, while the rear cuff 20 becomes inflated. With both cuffs gripping the colon wall a gentle retrograde traction is provided by pulling both the sheath and instrument so as to straighten the colon at least a few centimeters.

The next operating position resulting from the activation of foot switch 30 results in the rear cuff remaining inflated, while the front cuff deflates. The instrument 12 can now be advanced by pushing the instrument axially forward relative to the sheath 14 until resistance is encountered.

The operation of the device then repeats starting with step three and proceeding to the last step for each sequence until the forward end of the instrument 12 reaches the cecum.

To the extent described, the apparatus 10 is identical to the apparatus shown in the co-pending Lyddy et al. application, except that a different cuff assembly and means for providing air to the front and rear cuffs are provided in accordance with the present invention, and means are provided for selectively stiffening the sheath 14 in a safe and effective manner.

More specifically, the cuff assembly indicated generally at 40, is an integrally-formed element comprising the front section forming the front cuff 18 and the rear section forming the rear cuff 20. The middle section 42 connecting the front and rear cuff sections is shaped with expandable accordian folds so that the two cuffs can be moved relative to one another by a predetermined amount (typically about five inches) while the middle section conforms substantially to the shape of and covers that portion of the endoscopic instrument 12 disposed between the two cuffs. While the cuff assembly may be made of any one of several materials, the assembly is preferably made of a single molded sheet of thin urethane material capable of withstanding the necessary air pressures.

A support sheath 46 is secured to the front end of the instrument 12 for supporting the portion of the cuff assembly forming the front cuff 18. Means, such as the clamps 44a and 44b, secure the front and back parts of the front cuff 18 to the support sleeve so that the portion of the assembly forming the cuff can be inflated and evacuated without air leaking into the colon nor into the middle section 42 of the cuff assembly. In a similar manner means, such as the clamps 44c and 44d, secure the front and back parts of the rear cuff 20 to the front of the sheath so that the portion of the assembly forming the cuff can be inflated and evacuated without air leaking into the colon nor into the middle section 42 of the cuff assembly.

Figure 4:
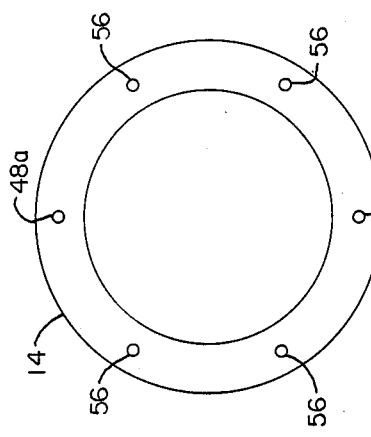
FIG. 4 is a cross-sectional radial view taken along line 4—4 in FIG. 3.

The apparatus described in the co-pending Lyddy et al. application is further modified to eliminate the air lines attached to the sheath 14 and instrument 12. More particularly, as shown in FIG. 4, at least two separate air passageways 48a and 48b (one for each cuff) are provided in the sheath 14. Air is provided to and from each cuff from air lines 24 (shown in FIG. 1) through these passageways. Air passageways 48a and 48b preferably extend through the sheath parallel to the center axis of the sheath. Passageway 48a extends from the rear end of the sheath 14 to the opening 50, the latter being in fluid communication with the rear cuff 18. The second air passageway 48b extends from the rear end of the sheath 14 through the sheath to the front end of the sheath where it is connected to the air line portion 24a. The latter is preferably a coiled line adapted to expand and contract with relative movement between the two cuffs and is disposed within and protected by the middle section 42. The front end of line portion 24a is connected to an air passageway 52 provided in the support sleeve 46 for supporting the front cuff 18. Air passageway 52 terminates at the opening 54, the latter being in fluid communication with the front cuff 18.

Finally, means are provided for selectively stiffening the sheath 14, when it is desirable to maneuver the instrument 12 through more difficult portions of the lumen, such as the sigmoid flexure. More particularly, the sheath 14 includes a plurality of passageways 56 provided in the wall of the sheath for receiving a pressurized fluid, such as water, so as to stiffen the sheath. The passageways 56 extend parallel to the center axis of the sheath. Interconnecting passageways may be provided within the sheath to transmit the pressurized fluid. Each passageway is diametrically opposed to another such passageway so that when pressurized fluid is provided the sheath will not distort or twist.

The apparatus 10 thus provides an improved instrument of the type described in the co-pending Lyddy et al. application. The cuff sections 18 and 20 are preferably made of urethane, which is more easily conformable to the supporting structure. The whole cuff assembly is made from a single molded sheet of plastic making it easily manufacturable. The support sleeve 46 and the sheath 14 are shaped to minimize interference when advancing the sheath alone or with the apparatus 12 through the lumen. The passageways 48a and 48b used to provide air to and from each of the cuffs are constructed to provide little or no interference with the movement of the instrument through the lumen of the body portion. The expandable middle portion 42 of the cuff assembly helps protect the portion of the instrument 12 in the space between the forward and rear cuffs so the portion will not become contaminated during use. The use of passageways 56 for receiving pressurized fluid provides safe and effective means for making the sheath and therefore the instrument, selectively more rigid so that the instrument can be passed through such body portions as the sigmoid flexure.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A device capable of being used with an elongated flexible instrument of the type adapted to at least partially extend into the lumen of a tubular body part and having a front end for leading said instrument through said lumen and a rear end opposite said front end, said device comprising, in combination:
    an elongated flexible sheath capable of being coaxially mounted on and axially slidable with respect to said instrument between said front and rear ends of said instrument;
    a cuff assembly including a front inflatable cuff section adapted to be secured to the front end of said instrument, a rear inflatable cuff section adapted to be secured to the front end of said sheath and a middle expandable section integrally formed with said front and rear cuff sections for protecting that portion of said instrument between the position of said front and rear cuffs;
    means for securing said front cuff section to said front end of said instrument so that said front cuff can be inflated with a pressurized fluid without introducing said pressurized fluid into said middle section;
    means for securing said rear cuff section to said front end of said sheath so that said rear cuff can be inflated with a pressurized fluid without introducing said pressurized fluid into said middle section; and
    means for providing said pressurized fluid to and from said front and rear cuff sections so as to selectively inflate and evacuate said cuff sections.

2. A device according to claim 1, wherein said front, rear and middle sections of said cuff assembly are made of an integrally-formed sheet of material.

3. A device according to claim 2, wherein said material is urethane.

4. A device according to claim 1, wherein said middle section includes accordian-like folds so as to expand or contract with relative movement between the front and rear cuff sections when said sheath and insturment slide relative to one another.

5. A device according to claim 1, wherein said means for securing said rear cuff section to said sheath includes a pair of clamps secured to opposite sides of said rear cuff section.

6. A device according to claim 1, wherein said means for securing said front cuff section to said instrument includes a support sleeve secured to said front end of said instrument, and means for securing said front cuff section to said support sleeve.

7. A device according to claim 6, wherein said means for securing said front cuff section to said support sleeve includes a pair of clamps secured to opposite sides of said front cuff section.

8. A device according to claim 1, wherein said means for providing pressurized fluid to and from said front and rear cuff sections includes a pair of passageways extending through the wall of said elongated sheath, one of said passageways having an opening in fluid communication with said rear cuff.

9. A device according to claim 8, wherein said means for securing said front cuff section to said instrument includes a support sleeve secured to said front end of said instrument, and means for securing said front cuff section to said support sleeve, and said means for providing pressurized fluid to and from said front and rear cuff sections includes a passageway formed in the wall of said support sleeve connected to the other of said passageways in said elongated sheath, and having an opening in fluid communication with said front cuff.

10. A device according to claim 9, wherein said means for providing pressurized fluid to and from said front and rear cuff sections includes an expandable air line connected between the passageway formed in the wall of said support sleeve and said other of said passageways in said elongated sheath.

11. A device according to claim 10, wherein said expandable air line is disposed within said middle section of said cuff assembly.

12. A device according to claim 1, further including means for selectively stiffening said elongated sheath.

13. A device according to claim 12, wherein said means for selectively stiffening said elongated sheath includes passageways disposed in the wall of said sheath for receiving a pressurized fluid.

* * * * *